United States Patent
Ul Ain et al.

(10) Patent No.: US 11,244,761 B2
(45) Date of Patent: Feb. 8, 2022

(54) ACCELERATED CLINICAL BIOMARKER PREDICTION (ACBP) PLATFORM

(71) Applicant: Accenture Global Solutions Limited, Dublin (IE)

(72) Inventors: Qurrat Ul Ain, Dublin (IE); Christina Gunther, Cambridge (GB)

(73) Assignee: Accenture Global Solutions Limited, Dublin (IE)

(*) Notice: Subject to any disclaimer, the term of this patent is extended or adjusted under 35 U.S.C. 154(b) by 696 days.

(21) Appl. No.: 15/816,957

(22) Filed: Nov. 17, 2017

(65) Prior Publication Data
US 2019/0156946 A1    May 23, 2019

(51) Int. Cl.
| | | |
|---|---|---|
| *G16H 50/20* | (2018.01) | |
| *G06N 3/08* | (2006.01) | |
| *G06N 3/04* | (2006.01) | |
| *G16B 40/00* | (2019.01) | |
| *G16B 20/00* | (2019.01) | |

(Continued)

(52) U.S. Cl.
CPC ............ *G16H 50/20* (2018.01); *G06N 3/04* (2013.01); *G06N 3/08* (2013.01); *G16B 20/00* (2019.02); *G16B 40/00* (2019.02); *G16B 40/10* (2019.02); *G16B 40/20* (2019.02)

(58) Field of Classification Search
CPC ........ G16H 50/20; G16B 40/00; G16B 40/10; G16B 20/10; G16B 40/20; G16B 20/00; G06N 3/04; G06N 3/08
See application file for complete search history.

(56) References Cited

U.S. PATENT DOCUMENTS

| | | | |
|---|---|---|---|
| 2005/0119534 A1* | 6/2005 | Trost ............... | G16H 20/60 600/300 |
| 2008/0201280 A1* | 8/2008 | Martin ............ | G06N 20/00 706/12 |

(Continued)

FOREIGN PATENT DOCUMENTS

JP    2016148604 A    8/2016

OTHER PUBLICATIONS

Huang, et.al., More Is Better: Recent Progress In Multi-Omics Data Integration Methods, Frontiers in Genetics, (Jun. 2017), vol. 8: pp. 1-12.*

(Continued)

*Primary Examiner* — Robert A Sorey
*Assistant Examiner* — Kimberly A. Sass
(74) *Attorney, Agent, or Firm* — Harrity & Harrity, LLP

(57) ABSTRACT

A device may receive medical data associated with potential patients for a clinical trial of a drug, where the medical data includes one or more of multi-omics data associated with the potential patients, genomic profiles of the potential patients, dosage and time associated with the drug, electronic medical records of the potential patients, or clinical trial data associated with the drug. The device may perform, in parallel, a topological data analysis, a non-matrix factorization analysis, and a neural network analysis of the medical data. The device may identify a group of patients, of the potential patients, for the clinical trial of the drug based on performing the topological data analysis, the non-matrix factorization analysis, and the neural network analysis of the medical data, and may provide information identifying the group of patients.

24 Claims, 9 Drawing Sheets

(51) Int. Cl.
  *G16B 40/10* (2019.01)
  *G16B 40/20* (2019.01)

(56) References Cited

U.S. PATENT DOCUMENTS

| | | | |
|---|---|---|---|
| 2013/0218581 A1 | 8/2013 | Catlett et al. | |
| 2014/0129259 A1* | 5/2014 | Seriani | G16H 40/67 705/3 |
| 2016/0203287 A1* | 2/2016 | Chen et al. | G16H 50/30 |
| 2018/0018424 A1 | 1/2018 | Horimoto et al. | |
| 2018/0046755 A1* | 2/2018 | Pe'er et al. | G06F 19/24 |

OTHER PUBLICATIONS

Zong, et.al. Multi-View Clustering Via Multi-Manifold Regulized Non-Negative Matrix Factorization, Neural Networks, (Feb. 2017) vol. 88: pp. 74-89.*

Kipf, et.al., "Variational Graph Auto-Encoders", (Nov. 2016, pp. 1-3), (arXiv:1611.07308v1[stat.ML]) (Year: 2016).*

Rashid, et.al., Dhaka: "Variational Autoencoder For Unmasking Tumor Heterogenity From Single Cell Genomic Data", (Sep. 4, 2017), pp. 1-17), dx.doi.org/10.1101/183863). (Year: 2017).*

Azuaje F., "Computational Models for Predicting Drug Responses in Cancer Research," Briefings in Bioinformatics, Jul. 2016, vol. 18 (5), pp. 820-829. XP055575877.

Extended European Search Report for Application No. EP18206424. 6, dated Apr. 29, 2019, 13 pages.

Gligorijevic V., et al., "Integrative Methods for Analyzing Big Data in Precision Medicine," Proteomics, Mar. 2016, vol. 16 (5), pp. 741-758. XP055576310.

Hidalgo S.J.T., et al., "A Master Pipeline for Discovery and Validation of Biomarkers," Image Analysis and Recognition: 11th International Conference, ICIAR 2014, Vilamoura, Portugal, Oct. 22-24, 2014, Proceedings, Part I; in: Lecture Notes in Computer Science, Dec. 2016, vol. 8814, XP047365025.

Tebani A., et al., "Clinical Metabolomics: The New Metabolic Window for Inborn Errors of Metabolism Investigations in the Post-Genomic Era," International Journal of Molecular Sciences, Jul. 2016, vol. 17 (7), pp. 1167. XP055576641.

Tebani A., et al., "Omics-Based Strategies in Precision Medicine: Toward a Paradigm Shift in Inborn Errors of Metabolism Investigations," International Journal of Molecular Sciences, Sep. 2016, vol. 17 (9), pp. E1555. XP055576307.

Ayasdi, Inc., "Topology and Topological Data Analysis," 2014, 10 pages.

* cited by examiner

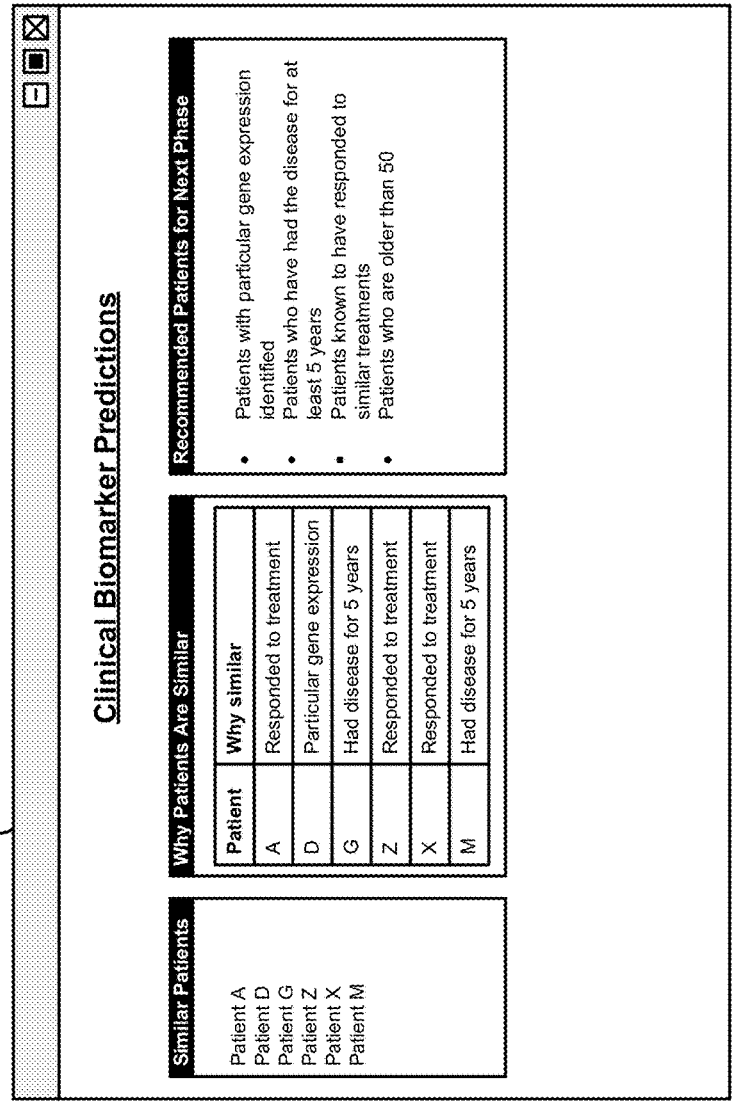
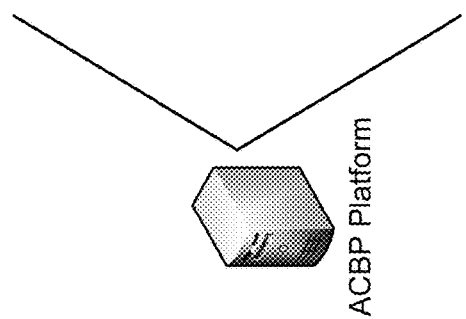
FIG. 1F

ACCELERATED CLINICAL BIOMARKER PREDICTION (ACBP) PLATFORM

BACKGROUND

A biomarker is a characteristic that is objectively measured and evaluated as an indicator of normal biological processes, pathogenic processes, or pharmacologic responses to a therapeutic intervention. The existing procedure for Food and Drug Administration (FDA) approval (e.g., clinical trials) of a drug is complex and a big challenge for pharmaceutical companies. Clinical trials require patient selection and need to identify correct patients and biomarkers for the clinical trials. Pharmaceutical companies and similar entities attempt to select the best patients and biomarkers for a particular drug undergoing clinical trials.

SUMMARY

In some implementations, a device may include one or more memories, and one or more processors, communicatively coupled to the one or more memories, to receive medical data associated with potential patients for a clinical trial of a drug, where the medical data includes one or more of multi-omics data associated with the potential patients, genomic profiles of the potential patients, dosage and time associated with the drug, electronic medical records of the potential patients, or clinical trial data associated with the drug. The one or more processors may perform, in parallel, a topological data analysis, a non-matrix factorization analysis, and a neural network analysis of the medical data, may identify a group of patients, of the potential patients, for the clinical trial of the drug based on performing the topological data analysis, the non-matrix factorization analysis, and the neural network analysis of the medical data, and may provide information identifying the group of patients.

In some implementations, a non-transitory computer-readable medium may store instructions that include one or more instructions that, when executed by one or more processors, cause the one or more processors to receive medical data associated with potential patients for a clinical trial of a drug, where the medical data includes at least two of multi-omics data associated with the potential patients, genomic profiles of the potential patients, dosage and time associated with the drug, electronic medical records of the potential patients, or clinical trial data associated with the drug. The one or more instructions may further cause the one or more processors to perform a topological data analysis, a non-matrix factorization analysis, and a neural network analysis of the medical data, where at least two of the topological data analysis, the non-matrix factorization analysis, or the neural network analysis of the medical data to be performed in parallel, identify a group of patients, of the potential patients, for the clinical trial of the drug, where the group of patients being identified based on consensus results generated by performing the topological data analysis, the non-matrix factorization analysis, and the neural network analysis of the medical data, and provide information identifying the group of patients.

In some implementations, a method may include receiving, by a device, medical data associated with potential patients for a clinical trial of a drug, where the medical data includes one or more of multi-omics data associated with the potential patients, genomic profiles of the potential patients, dosage and time associated with the drug, electronic medical records of the potential patients, or clinical trial data associated with the drug. The method may include preprocessing, by the device, the medical data to generate normalized and dimensionally reduced medical data, and performing, by the device and in parallel, a topological data analysis, a non-matrix factorization analysis, and a neural network analysis of the normalized and dimensionally reduced medical data. The method may include identifying, by the device, a group of patients, of the potential patients, for the clinical trial of the drug based on performing the topological data analysis, the non-matrix factorization analysis, and the neural network analysis of the normalized and dimensionally reduced medical data, and providing, by the device, information identifying the group of patients.

BRIEF DESCRIPTION OF THE DRAWINGS

FIGS. 1A-1F are diagrams of an overview of an example implementation described herein;

DETAILED DESCRIPTION

The following detailed description of example implementations refers to the accompanying drawings. The same reference numbers in different drawings may identify the same or similar elements.

An early phase of a clinical trial usually includes a small number of recruited patients. Identification of biomarkers and patients that are non-responsive to a drug becomes a challenge with such a small number of patients. Furthermore, the initial phases of a clinical trial usually do not have a specific patient selection criterion, which results in the recruitment of wrong types of patients and hence an increase in the cost of the clinical trial. This eventually results in a reduction in the likelihood of approval of a drug.

Some implementations described herein provide an accelerated clinical biomarker prediction (ACBP) platform that determines patient profiles that are likely to respond well to a drug, and tailors clinical trials to target patients with the responsive profiles. The ACBP platform may utilize genomic profiles and electronic medical record (EMR) data of potential patients to identify clinical biomarkers in pre-clinical trial and post-clinical trial settings. The ACBP platform may identify profiles of responsive patient subgroups during clinical trials, may accelerate new drug application (NDA) submissions, may reduce liability due to more informed decision making, may reduce clinical trial cost, may improve patient compliance, may conserve resources (e.g., medical resources, equipment resource, etc.) that would be used to duplicate failed clinical trials due to incorrect patient selection, may improve the clinical trial process, and/or the like.

Figure 1A:
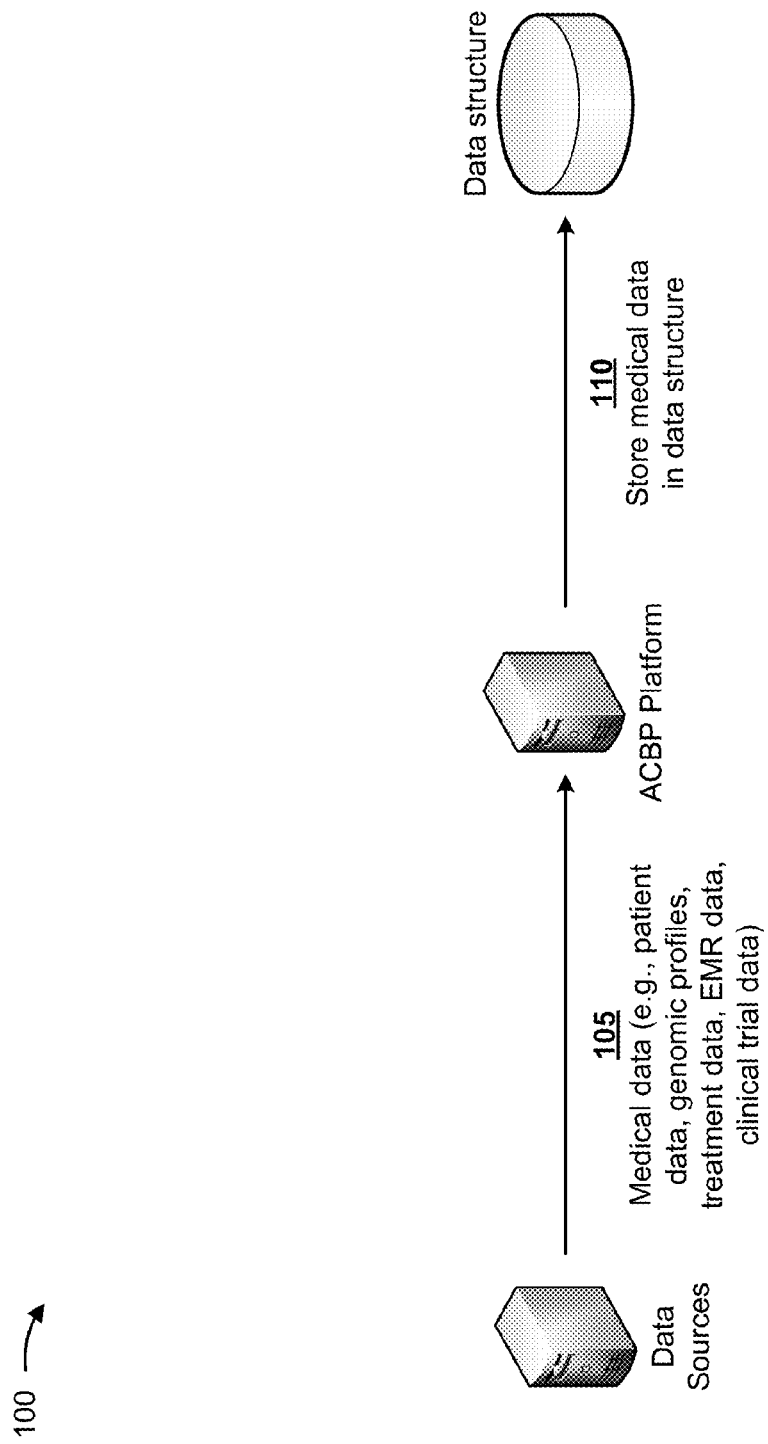

FIGS. 1A-1F are diagrams of an overview of an example implementation 100 described herein. As shown in FIG. 1A, multiple data sources may be associated with an ACBP platform. As shown in FIG. 1A, by reference number 105, the data sources may provide medical data to the ACBP platform, and the ACBP platform may receive the medical data. In some implementations, the medical data may include data associated with a drug that needs to undergo a clinical trial, medical data associated with potential patients for the clinical trial, and/or the like. In some implementations, the medical data may include one or more of multiomics data (e.g., genomics data such as gene expression data, proteomics data such as protein data, metabolomics data such as metabolic data, and/or the like) associated with the potential patients, genomic profiles (e.g., mutation profiles, gene on or off states, and/or the like) of the potential patients, dosage and time (e.g., how often to take the drug) associated with the drug, EMR data of the potential patients, prior clinical trial data of the drug (e.g., adverse effects of the drug, clinical trial data of the drug from different geographical locations, and/or the like), and/or the like.

In some implementations, the data sources may provide the medical data to the ACBP platform in a variety of formats, and the ACBP platform may convert the variety of formats to a particular format. In some implementations, the data sources may convert the medical data to the particular format, and may provide the medical data to the ACBP platform in the particular format. In some implementations, the ACBP platform may automatically retrieve the medical data from the data sources. In some implementations, the ACBP platform may provide security features (e.g., encryption, firewalls, and/or the like) so that confidential medical data may be securely provided by the data sources to the ACBP platform.

As further shown in FIG. 1A, and by reference number 110, the ACBP platform may store the medical data in a data structure, such as a database, a table, a linked-list, a tree, and/or the like. In some implementations, the data structure may be provided in a memory associated with the ACBP platform. The ACBP platform may store the medical data so that the ACBP platform may perform further processing on the medical data, such as determining patient profiles that are likely to respond well to the drug, and tailoring clinical trials to target patients with the patient profiles. In some implementations, the data structure may include a secure data structure that protects the confidential nature of the medical data.

Figure 1B:
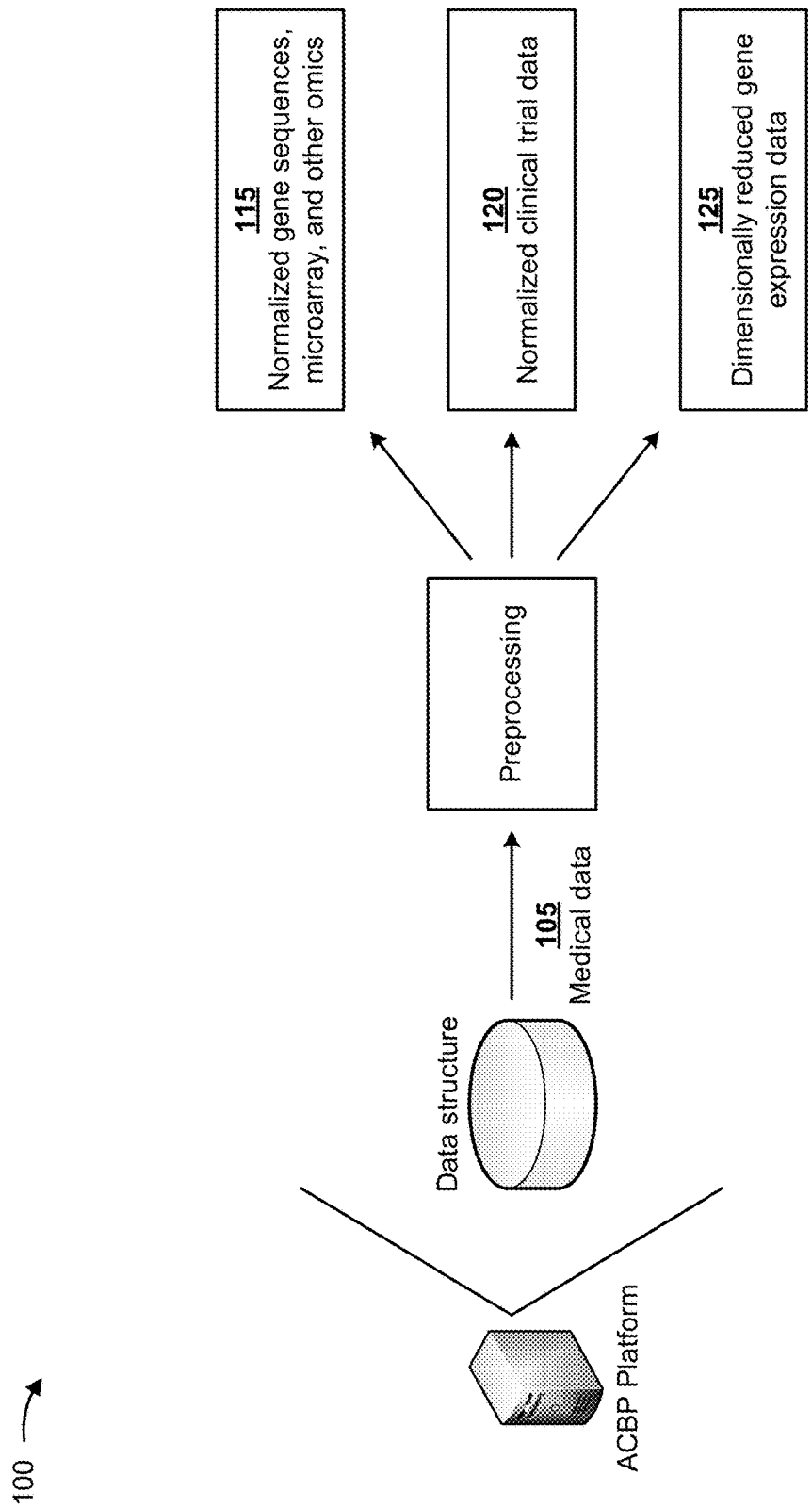

As shown in FIG. 1B, a preprocessing function, provided by the ACBP platform, may retrieve or receive the medical data from the data structure, as indicated by reference number 105. In some implementations, the preprocessing function may process the medical data using natural language processing. In this case, preprocessing function may include or be associated with a natural language processing application that recognizes, parses, and/or interprets the medical data. Natural language processing is a field of computer science, artificial intelligence, and/or computational linguistics concerned with the interactions between computers and human (natural) languages and, in some cases, may be particularly concerned with programming computers to fruitfully process large natural language corpora.

In some implementations, the preprocessing function may normalize the medical data by changing the medical data from different formats to a particular format (e.g., changing text to numbers), combining portions of the medical data (e.g., combining redundant data), and/or the like. In some implementations, the medical data may include a format (e.g., gene microarray images), and the preprocessing function may convert the gene microarray images into numbers and may normalize the numbers.

In some implementations, if the medical data includes large dimensionality data (e.g., large dimensionality gene expression data), the preprocessing function may apply a dimensionality reduction technique to reduce the dimensions of the large dimensionality data (e.g., to a number of informative dimensions of the data). In some implementations, the dimensionality reduction technique may include a t-distributed stochastic neighbor embedding technique, an autoencoder technique, and/or the like. Reducing the dimensionality of the medical data may eliminate noise during further processing of the medical data, as described herein. In some implementations, the ACBP platform may process a large quantity of data items that cannot be processed objectively by a human actor.

As further shown in FIG. 1B, preprocessing of the medical data, by the ACBP platform, may generate normalized and/or dimensionally reduced medical data. For example, as shown by reference number 115, the preprocessing function may generate normalized gene sequences, gene microarray data, other omics data, and/or the like from the medical data. In another example, as shown by reference number 120, the preprocessing function may generate normalized clinical trial data, and/or the like from the medical data. In still another example, as shown by reference number 125, the preprocessing function may generate dimensionally reduced gene expression data, and/or the like from the medical data.

Figure 1C:
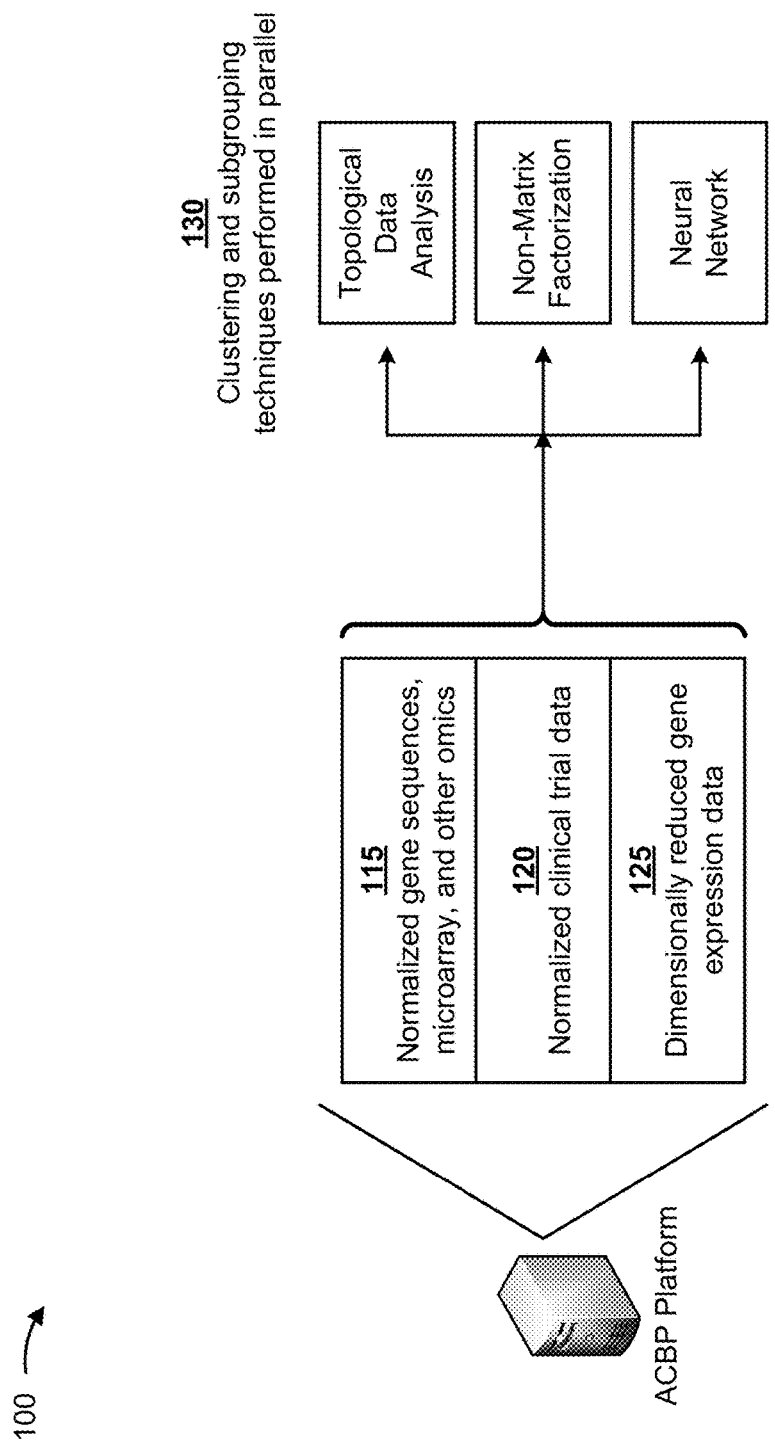

As shown in FIG. 1C, and by reference number 130, the ACBP platform may perform, in parallel, clustering and subgrouping techniques on the normalized and dimensionally reduced medical data (e.g., the normalized gene sequences, gene microarray data, and other omics data 115, the normalized clinical trial data 120, and the dimensionally reduced gene expression data 125). In some implementations, the ACBP platform may perform the clustering and subgrouping techniques on the normalized and dimensionally reduced medical data at separate times (e.g., not in parallel, although parallel performance may decrease a time associated with processing the normalized and dimensionally reduced medical data). In some implementations, the clustering and subgrouping techniques may include a topological data analysis technique, a non-matrix factorization technique, a neural network technique, and/or the like.

In some implementations, the topological data analysis technique may include a technique that utilizes selected metrics to determine a similarity between two nodes in a cluster (e.g., of patients), that is based on a shape or a topology of clusters, that combines a dimensionality reduction principal component analysis (PCA) technique with clustering to determine a similarity between samples (e.g., patients), and/or the like.

In some implementations, the non-matrix factorization technique may include an unsupervised learning approach for clustering of patient samples based on gene expression data. For example, the non-matrix factorization technique may include a non-negative matrix factorization technique that includes a group of processes in multivariate analysis and linear algebra where a matrix is factorized into two matrices, with a property that all three matrices have no negative elements. This non-negativity makes the resulting matrices easier to inspect.

In some implementations, the neural network technique may include a variational graph autoencoders technique that provides unsupervised learning on graph-structured data. The variational graph autoencoders technique may receive a graph convolutional network encoder as an input, and may provide a simple decoder as an output. For example, the variational graph autoencoders technique may select genomic and genetic features of the patients, and may utilize the genomic and genetic features of the patients to generate a graph structure of patient samples. The simple decoder may output information regarding a group of similar patients.

Figure 1D:
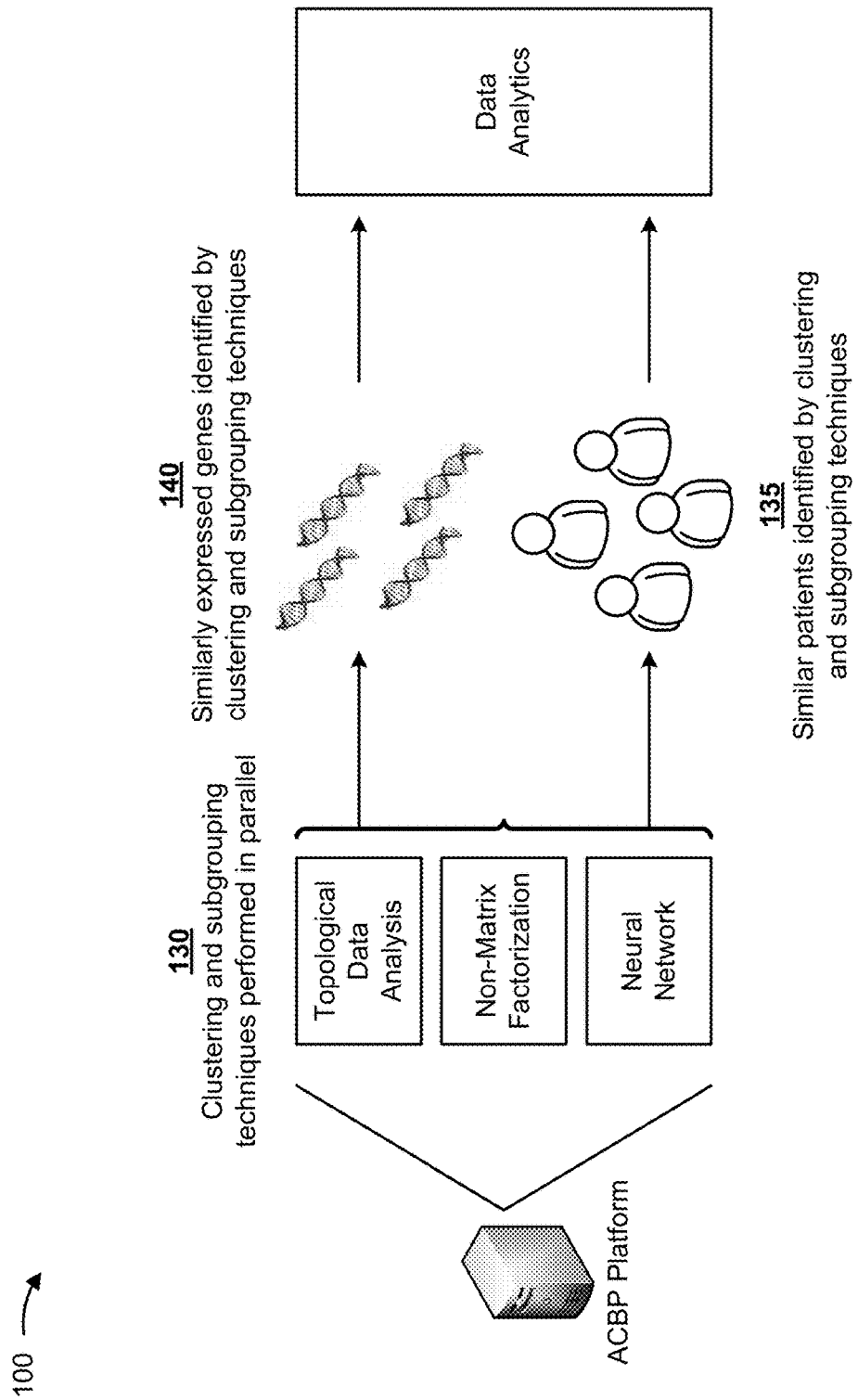

As shown in FIG. 1D, and by reference number 135, the ACBP platform may identify a group of similar patients, from the potential patients, based on performing the clustering and subgrouping techniques on the normalized and dimensionally reduced medical data. As further shown in FIG. 1D, and by reference number 140, the ACBP platform may identify a group of similarly expressed genes, from the potential patients, based on performing the clustering and subgrouping techniques on the normalized and dimensionally reduced medical data.

In some implementations, the identified group of similar patients and the identified group of similarly expressed genes may be determined based on a consensus of results generated by each of the topological data analysis technique, the non-matrix factorization technique, and the neural network technique. In some implementations, the ACBP platform may equally weight the results of each technique, and may combine (e.g., average) the results to determine the identified group of similar patients and the identified group of similarly expressed genes. In some implementations, the ACBP platform may apply different weights to the results of each technique, and may utilize the weighted results to determine the identified group of similar patients and the identified group of similarly expressed genes. For example, the ACBP platform may assign a first weight (e.g., 0.5) to the results obtained from the topological data analysis technique, may assign a second weight (e.g., 0.3) to the results obtained from the non-matrix factorization technique, and may assign a third weight (e.g., 0.2) to the results obtained from the neural network technique. Based on this example, when determining the identified group of similar patients and the identified group of similarly expressed genes, more weight may be given to the results obtained from the topological data analysis technique than to the results obtained from the non-matrix factorization technique and the results obtained from the neural network technique.

As further shown in FIG. 1D, the ACBP platform may provide information associated with the identified group of similar patients and the identified group of similarly expressed genes to a data analytics function of the ACBP platform. The data analytics function may process the information associated with the identified group of similar patients and the identified group of similarly expressed genes in order to determine reasons why the identified group of patients are similar.

Figure 1E:
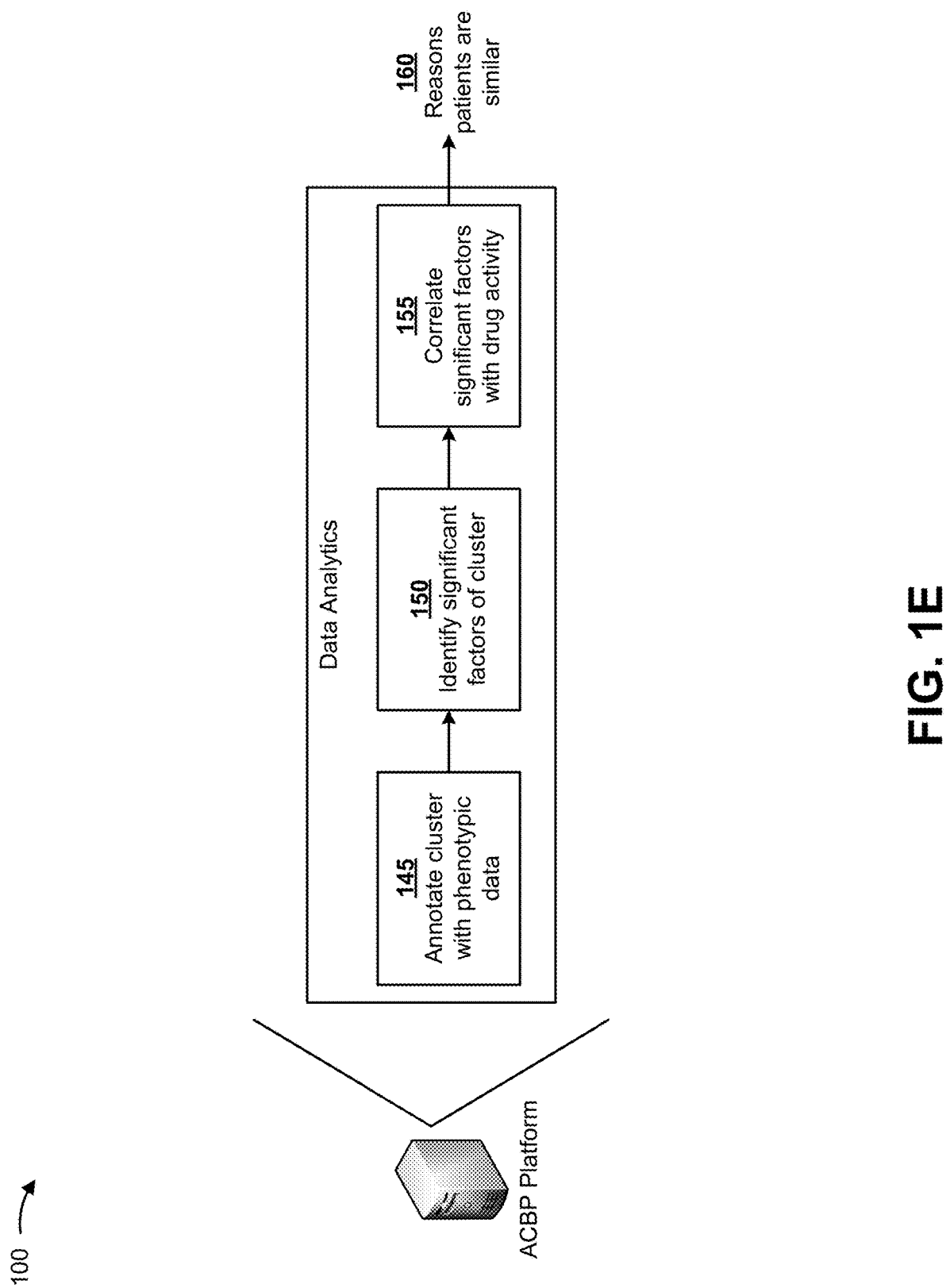

As shown in FIG. 1E, and by reference number 145, the data analytics function may annotate a cluster (e.g., the identified group of patients) with phenotypic data. For example, the data analytics function may associate relevant phenotypic data with the identified group of patients. In some implementations, the phenotypic data may include information associated with the identified group of similarly expressed genes, observable physical or biochemical characteristics of the identified group of patients as determined by genetic makeup and environmental influences, expressions of specific traits, such as stature or blood type, based on genetic and environmental influences, and/or the like.

As further shown in FIG. 1E, and by reference number 150, the data analytics function may identify significant factors, of the annotated cluster (e.g., the identified group of patients annotated with the phenotypic data), which are responsible for clustering. In some implementations, the data analytics function may utilize a feature extraction technique (e.g., a regression analysis, an elastic net regression analysis, or another supervised analysis) to identify the significant factors of the annotated cluster.

As further shown in FIG. 1E, and by reference number 155, the data analytics function may correlate the significant factors with activity of the drug. In some implementations, the activity of the drug may include a sensitivity to the drug by the identified group of patients, a resistant to the drug by the identified group of patients, and/or the like. In some implementations, the data analytics function may utilize a gene set enrichment analysis (e.g., a method to identify classes of genes or proteins that are over-represented in a large set of genes or proteins, and may have an association with disease phenotypes), a pathway set enrichment analysis (e.g., used to identify related proteins within a pathway or to build a new pathway from proteins of interest, and may be helpful when studying differential expression of a gene in a disease or analyzing an omics dataset with a large number of proteins), and/or the like to correlate the significant factors with activity of the drug.

As further shown in FIG. 1E, and by reference number 160, the data analytics function may provide information indicating reasons the identified group of patients are similar based on correlating the significant factors with activity of the drug. In some implementations, the ACBP platform may provide, for display, to a user of the ACBP platform, or to another device (e.g., a computing device associated with a pharmaceutical company), the information associated with the identified group of patients and/or the information indicating reasons the identified group of patients are similar.

As shown in FIG. 1F, and by reference number 165, the ACBP platform may provide (e.g., to a user or another device) a user interface that includes the information associated with the identified group of patients and/or the information indicating reasons the identified group of patients are similar. In some implementations, the user interface may provide information associated with a phenotypically-annotated group of patients (e.g., the identified group of patients), significant clinical biomarkers associated with the group of patients, new indications for the drug that were identified from the medical data. For example, the user interface may provide information indicating that patients A, D, G, Z, X, and M are similar, information indicating why these patients are similar (e.g., patients A, Z, and X responded to treatment, patient D had a particular gene expression, and patients G and M had a disease for five years), information providing recommended patients for a next phase of the clinical trials of the drug (e.g., patients with particular gene expression identified, patients who have had the disease for at least five years, patients known to have responded to similar treatments, patients who are older than fifty), and/or the like.

In some implementations, a user (e.g., a pharmaceutical company) of the ACBP platform may utilize information provided by the user interface to select patients for a next phase of the clinical trials of the drug. This may accelerate a NDA submission for the drug by the pharmaceutical company, may reduce liability for the pharmaceutical company due to more informed decision making, may reduce clinical trial cost for the pharmaceutical company, and may improve patient compliance.

In this way, the ACBP platform improves the performance of an entity (e.g., a pharmaceutical company and computing resources associated with the pharmaceutical company) by determining patient profiles that are likely to respond well to a drug, and enabling the entity to tailor clinical trials to target patients with the patient profiles. Further, the ACBP platform enables the entity to conserve computing resources (e.g., processor resources, memory resources, and/or the like) since the entity will not waste such computing resources attempting to perform multiple unnecessary clinical trials, handle liability issues associated with the drug, handle patient compliance, and/or the like.

As indicated above, FIGS. 1A-1F are provided merely as examples. Other examples are possible and may differ from what was described with regard to FIGS. 1A-1F.

Figure 2:
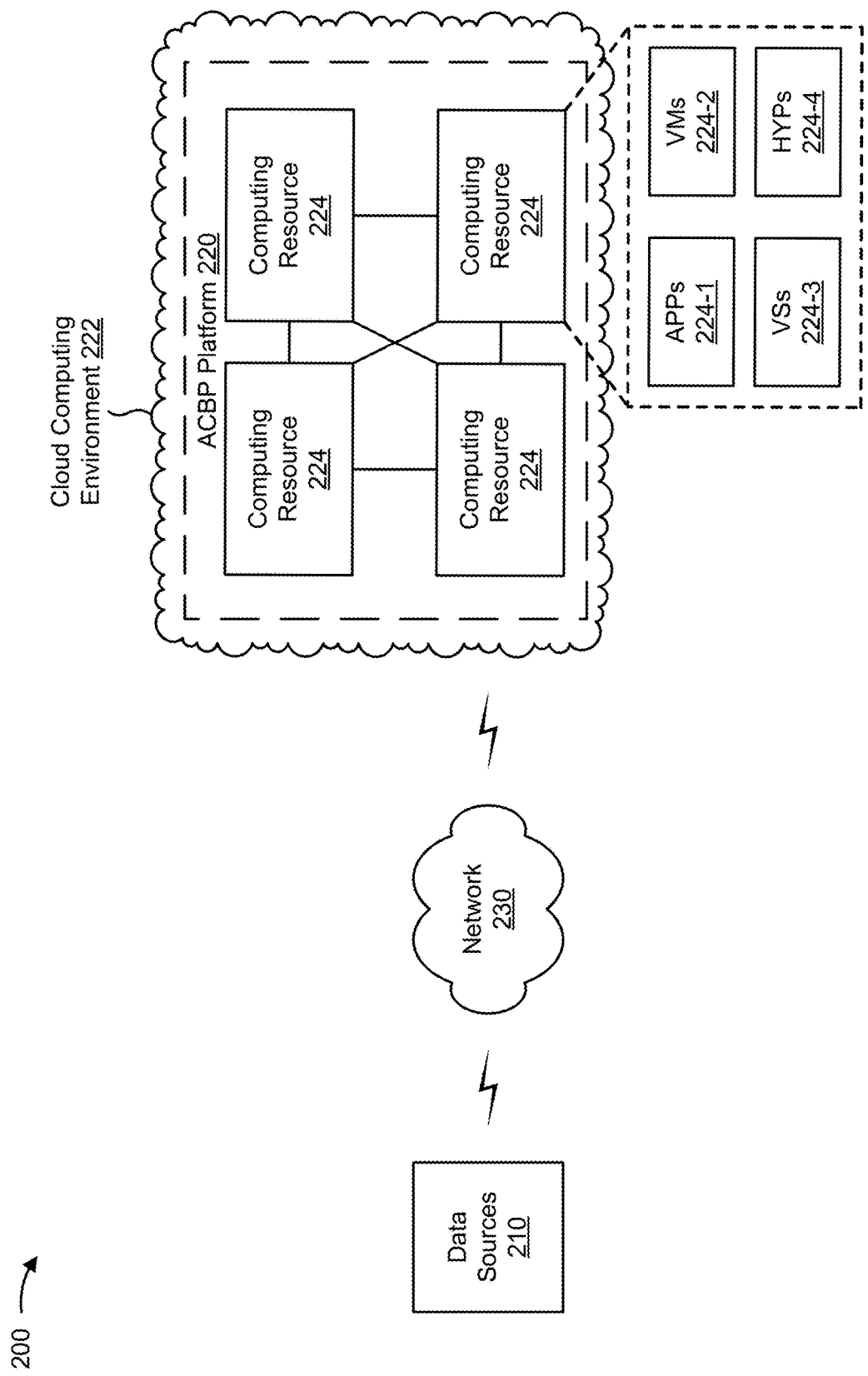
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include data sources 210, an ACBP platform 220, and a network 230. Devices of environment 200 may interconnect via wired connections, wireless connections, or a combination of wired and wireless connections.

Data source 210 includes one or more devices capable of receiving, generating, storing, processing, and/or providing information, such as information described herein. For example, data source 210 may include a computing device, such as a server device, a desktop computer, a laptop computer, a tablet computer, a handheld computer, a mobile phone (e.g., a smart phone, a radiotelephone, etc.), an imaging device, a wearable communication device (e.g., a smart wristwatch, a pair of smart eyeglasses, etc.), a medical device, or a similar type of device. In some implementations, data source 210 may receive information from and/or transmit information to ACBP platform 220. In some implementations, data source 210 may provide medical data, such as multi-omics patient data (e.g., gene expression data, levels of gene expression data, metabolic data, and/or the like), genomic profiles (e.g., a mutation profile in a patient, a gene on or off state in a patient, and/or the like), drug dosage and time data, electronic medical record (EMR) data, clinical trial data (e.g., adverse effects of a drug, clinical trial data from different locations and giving different results, and/or the like), and/or the like, to ACBP platform 220.

In some implementations, data source 210 may be associated with an entity (e.g., a pharmaceutical company) that is attempting to get a drug approved by the FDA. In some implementations, data source 210 may be associated with a patient that is participating in a clinical trial of the drug. In some implementations, data source 210 may be associated with other entities (e.g., government agencies, academics institutions, and/or the like).

ACBP platform 220 includes one or more devices that determine a patient profile of a patient that is likely to respond well to a drug, and tailor clinical trials to target patients with the patient profile. In some implementations, ACBP platform 220 may be designed to be modular such that certain software components may be swapped in or out depending on a particular need. As such, ACBP platform 220 may be easily and/or quickly reconfigured for different uses. In some implementations, ACBP platform 220 may receive information from and/or transmit information to one or more data sources 210.

In some implementations, as shown, ACBP platform 220 may be hosted in a cloud computing environment 222. Notably, while implementations described herein describe ACBP platform 220 as being hosted in cloud computing environment 222, in some implementations, ACBP platform 220 may not be cloud-based (i.e., may be implemented outside of a cloud computing environment) or may be partially cloud-based.

Cloud computing environment 222 includes an environment that hosts ACBP platform 220. Cloud computing environment 222 may provide computation, software, data access, storage, etc. services that do not require end-user knowledge of a physical location and configuration of system(s) and/or device(s) that hosts ACBP platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host ACBP platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by data source 210. Application 224-1 may eliminate a need to install and execute the software applications on data source 210. For example, application 224-1 may include software associated with ACBP platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., an operator of ACBP platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
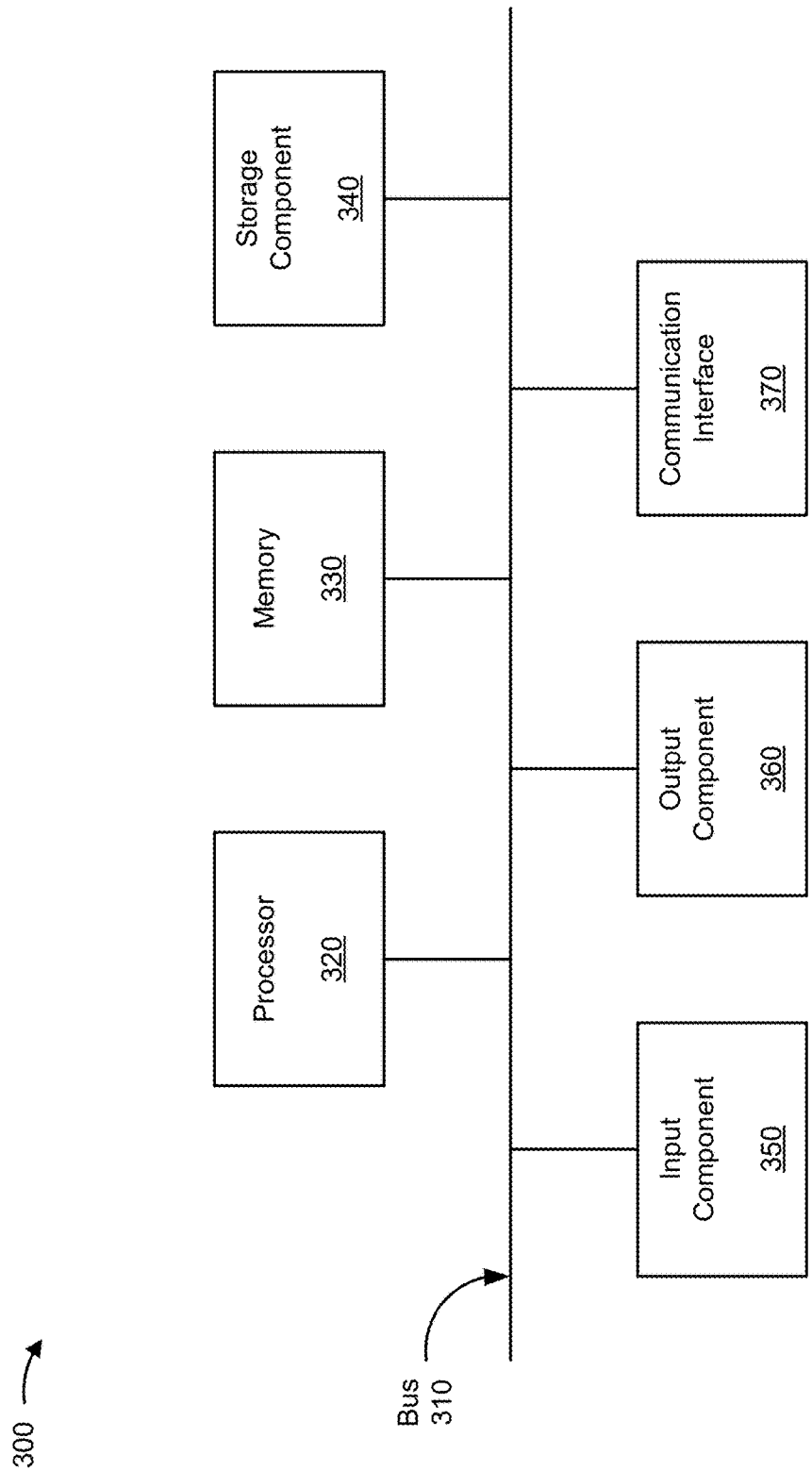
FIG. 3 is a diagram of example components of one or more devices of FIG. 2.

FIG. 3 is a diagram of example components of a device 300. Device 300 may correspond to data source 210, ACBP platform 220, and/or computing resource 224. In some implementations, data source 210, ACBP platform 220, and/or computing resource 224 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 takes the form of a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
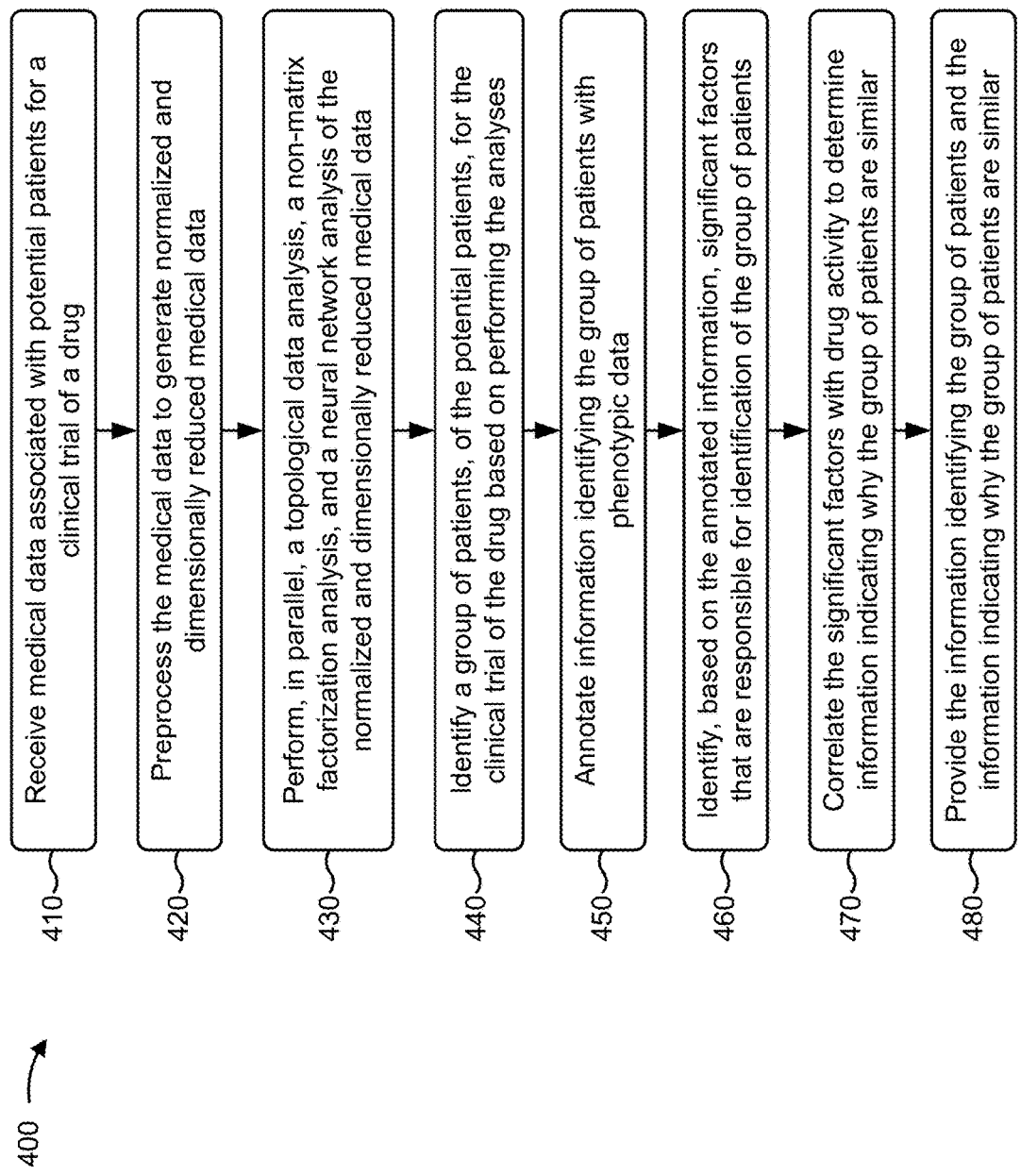
FIG. 4 is a flow chart of an example process for identifying patients for clinical trials of a drug.

FIG. 4 is a flow chart of an example process 400 for identifying patients for clinical trials of a drug. In some implementations, one or more process blocks of FIG. 4 may be performed by ACBP platform 220. In some implementations, one or more process blocks of FIG. 4 may be performed by another device or a group of devices separate from or including ACBP platform 220, such as data source 210.

As shown in FIG. 4, process 400 may include receiving medical data associated with potential patients for a clinical trial of a drug (block 410). For example, ACBP platform 220 may receive medical data associated with potential patients for a clinical trial of a drug. In some implementations, data source 210 may provide the medical data to ACBP platform 220, and ACBP platform 220 may receive the medical data from data source 210, as described above in connection with FIG. 1A. In some implementations, the medical data may include one or more of multi-omics data (e.g., genomics data such as gene expression data, proteomics data such as protein data, metabolomics data such as metabolic data, and/or the like) associated with the potential patients, genomic profiles (e.g., mutation profiles, gene on or off states, and/or the like) of the potential patients, dosage and time (e.g., how often to take the drug) associated with the drug, EMR data of the potential patients, prior clinical trial data of the drug (e.g., adverse effects of the drug, clinical trial data of the drug from different geographical locations, and/or the like), and/or the like. In some implementations, ACBP platform 220 may need only one of the multi-omics data, the genomic profiles, the dosage and time associated with the drug, the EMR data, or the prior clinical trial data in order to identify patients for clinical trials of the drug. In some implementations, the medical data may include a quantity of data items that cannot be processed objectively by a human actor.

In some implementations, ACBP platform 220 may receive medical data from a plurality of disparate and/or heterogeneous data sources 210. For example, ACBP platform 220 may receive the multi-omics data from data sources 210 associated with a pharmaceutical company, an entity performing clinical trials, the patients, and/or the like; may receive the genomic profiles from data sources 210 associated with a pharmaceutical company, an entity performing clinical trials, the patients, and/or the like; may receive the EMR data from data sources 210 associated with the patients; may receive the prior clinical trials from data sources 210 associated with a pharmaceutical company, an entity performing clinical trials, and/or the like; and/or the like.

In this way, ACBP platform 220 may receive medical data associated with potential patients for a clinical trial of a drug.

As further shown in FIG. 4, process 400 may include preprocessing the medical data to generate normalized and dimensionally reduced medical data (block 420). For example, ACBP platform 220 may preprocess the medical data to generate normalized and dimensionally reduced medical data, as described above in connection with FIG. 1B. In some implementations, ACBP platform 220 may process the medical data using natural language processing. In some implementations, ACBP platform 220 may normalize the medical data by changing the medical data from different formats to a particular format (e.g., changing text to numbers), combining portions of the medical data (e.g., combining redundant data), and/or the like. In some implementations, if the medical data includes large dimensionality data, ACBP platform 220 may apply a dimensionality reduction technique to reduce the dimensions of the large dimensionality data (e.g., to a number of informative dimensions of the data). In some implementations, the preprocessing of the medical data, by ACBP platform 220, may generate normalized and/or dimensionally reduced medical data.

In this way, ACBP platform 220 may preprocess the medical data to generate normalized and dimensionally reduced medical data.

As further shown in FIG. 4, process 400 may include performing, in parallel, a topological data analysis, a non-matrix factorization analysis, and a neural network analysis of the normalized and dimensionally reduced medical data (block 430). For example, ACBP platform 220 may perform, in parallel, a topological data analysis, a non-matrix factorization analysis, and a neural network analysis of the normalized and dimensionally reduced medical data, as described above in connection with FIG. 1C. In some implementations, the topological data analysis technique may include a technique that utilizes selected metrics to determine a similarity between two nodes in a cluster, that is based on a shape or a topology of clusters, and that combines a dimensionality reduction PCA technique with clustering to determine a similarity between samples (e.g., patients). In some implementations, the non-matrix factorization analysis technique may include an unsupervised learning approach for clustering of patient samples based on gene expression data. In some implementations, the neural network analysis technique may include a variational graph autoencoders technique that provides unsupervised learning on graph-structured data.

In some implementations, the topological data analysis technique may determine a similarity between a first patient and a second patient, of the potential patients, based on graph analysis. In some implementations, the non-matrix factorization analysis technique may determine a cluster of similar patients, of the potential patients, based on a similarity of elements in a matrix. In some implementations, the neural network analysis technique may determine a similarity between a first patient and a second patient, of the potential patients, based on a comparison between an input layer and a hidden layer of a neural network. A neural network may be formed in three layers called an input layer, a hidden layer, and an output layer. Each layer may include one or more nodes, and lines between the nodes may indicate a flow of information from one node to a next node. The nodes of the input layer may be passive and may not modify the information. The nodes of the hidden layer and the output layer may be active and may modify the information. The hidden layer may be provided between the input layer and the output layer of the neural network.

In this way, ACBP platform 220 may perform, in parallel, a topological data analysis, a non-matrix factorization analysis, and a neural network analysis of the normalized and dimensionally reduced medical data.

As further shown in FIG. 4, process 400 may include identifying a group of patients, of the potential patients, for the clinical trial of the drug based on performing the analyses (block 440). For example, ACBP platform 220 may identify a group of patients, of the potential patients, for the clinical trial of the drug based on performing the analyses, as described above in connection with FIG. 1D. In some implementations, the identified group of patients may be determined based on a consensus of results generated by each of the topological data analysis technique, the non-matrix factorization technique, and the neural network technique. In some implementations, ACBP platform 220 may equally weight the results of each technique, and may combine the results to determine the identified group of patients. In some implementations, ACBP platform 220 may apply different weights to the results of each technique, and may utilize the weighted results to determine the identified group of patients. In some implementations, ACBP platform 220 may identify the group of patients by comparing outputs of the topological data analysis, the non-matrix factorization analysis, and the neural network analysis to identify clusters of patients which are similar.

In some implementations, ACBP platform 220 may generate a ranked list of patients in the identified group of patients based on the results of each technique. For example, ACBP platform 220 may assign scores and weights to factors used to identify the identified group of patients, and may generate a total score for each patient in the identified group of patients based on the scores and weights. A greater total score may provide an indication that a patient is associated with more factors used to identify the identified group of patients. A lower total score may provide an indication that a patient is associated with less factors used to identify the identified group of patients. ACBP platform 220 may rank the patients in the identified group of patients based on the total scores, and may provide a ranked list of the identified group of patients.

In some implementations, ACBP platform 220 may train a model (e.g., the topological data analysis technique, the non-matrix factorization technique, the neural network technique, a model that combines the results of these techniques, and/or the like) to generate a score for each patient in the identified group of patients (e.g., where a score may relate to a measure of candidacy of a patient to be a candidate for a clinical trial of the drug, so that a higher score may indicate a better candidate for the clinical trial). In some implementations, the model may output a ranked list of a top predetermined quantity of candidate patients, a list of candidate patients with scores over a threshold score, a list of candidate patients until a score of one candidate patient is at least a threshold higher than a score of a next candidate patient in a ranked list, and/or the like.

In this way, ACBP platform 220 may identify a group of patients, of the potential patients, for the clinical trial of the drug based on performing the analyses.

As further shown in FIG. 4, process 400 may include annotating information identifying the group of patients with phenotypic data (block 450). For example, ACBP platform 220 may annotate information identifying the group of patients with phenotypic data, as described above in connection with FIG. 1E. In some implementations, ACBP platform 220 may associate relevant phenotypic data with the identified group of patients. In some implementations, the phenotypic data may include information associated with the identified group of similarly expressed genes, observable physical or biochemical characteristics of the identified group of patients as determined by genetic makeup and environmental influences, expressions of specific traits, such as stature or blood type, based on genetic and environmental influences, and/or the like.

In some implementations, ACBP platform 220 may identify the relevant phenotypic data from the medical data received by ACBP platform 220, and may associate the relevant phenotypic data with the identified group of patients. In such implementations, may train a model (e.g., the topological data analysis technique, the non-matrix factorization technique, the neural network technique, a model that combines the results of these techniques, and/or the like) to generate a score for each portion of the medical data used to determine each patient in the identified group of patients (e.g., where a score may relate to a utilization of the portion of the medical data in determining whether a patient is a candidate for a clinical trial of the drug, so that a higher score may indicate a higher utilization of the portion of the medical data). In some implementations, the model may output a ranked list of a top portions of the medical data, a list of portions of the medical data with scores over a threshold score, a list of portions of the medical data until a score of one portion of the medical data is at least a threshold higher than a score of a next portion of the medical data in a ranked list, and/or the like.

In some implementations, ACBP platform 220 may identify the relevant phenotypic data based on another technique or combination of techniques. In some implementations, ACBP platform 220 may receive the phenotypic data separately from the medical data (e.g., from data sources 210 that are different than data sources 210 associated with the medical data), and may identify the relevant phenotypic data based on the model described above.

In this way, ACBP platform 220 may annotate information identifying the group of patients with phenotypic data.

As further shown in FIG. 4, process 400 may include identifying, based on the annotated information, significant factors that are responsible for identification of the group of patients (block 460). For example, ACBP platform 220 may identify, based on the annotated information, significant factors that are responsible for identification of the group of patients, as described above in connection with FIG. 1E. In some implementations, ACBP platform 220 may utilize a feature extraction technique (e.g., a regression analysis, an elastic net regression analysis, or other supervised analyses) to identify the significant factors based on the annotated information (e.g., information identifying the group of patients, as annotated with the phenotypic data).

In some implementations, ACBP platform 220 may utilize a regression analysis to estimate relationships among the annotated information identifying the group of patients, and to identify the significant factors based on the relationships. The regression analysis may include techniques for modeling and analyzing several variables (e.g. provided by the annotated information identifying the group of patients) that focus on a relationship between a dependent variable and one or more independent variables or predictors. The regression analysis may determine how a typical value of the dependent variable (e.g., a criterion variable) changes when any one of the independent variables is varied and while the other independent variables are held fixed. The regression analysis may estimate a conditional expectation of the dependent variable given the independent variables (e.g., an average value of the dependent variable when the independent variables are fixed).

In this way, ACBP platform 220 may identify, based on the annotated information, significant factors that are responsible for identification of the group of patients.

As further shown in FIG. 4, process 400 may include correlating the significant factors with drug activity to determine information indicating why the group of patients are similar (block 470). For example, ACBP platform 220 may correlate the significant factors with drug activity to determine information indicating why the group of patients are similar, as described above in connection with FIG. 1E. In some implementations, the activity of the drug may include a sensitivity to the drug by the identified group of patients, a resistance to the drug by the identified group of patients, and/or the like. In some implementations, ACBP platform 220 may utilize a gene set enrichment analysis, a pathway set enrichment analysis, and/or the like to correlate the significant factors with activity of the drug. The gene set enrichment analysis may include a technique to identify classes of genes or proteins that are over-represented in a large set of genes or proteins, and may have an association with disease phenotypes. The pathway set enrichment analysis may include a technique to identify related proteins within a pathway or to build a new pathway from proteins of interest, and may be helpful when studying differential expression of a gene in a disease or analyzing an omics dataset with a large number of proteins.

In this way, ACBP platform 220 may correlate the significant factors with drug activity to determine information indicating why the group of patients are similar.

As further shown in FIG. 4, process 400 may include providing the information identifying the group of patients and the information indicating why the group of patients are similar (block 480). For example, ACBP platform 220 may provide information identifying the group of patients and the information indicating why the group of patients are similar, as described above in connection with FIGS. 1E and 1F. In some implementations, ACBP platform 220 may provide, for display, to a user of ACBP platform 220, or to another device (e.g., a computing device associated with a pharmaceutical company), the information associated with the identified group of patients and/or the information indicating reasons the identified group of patients are similar.

In some implementations, ACBP platform 220 may provide (e.g., to a user or another device) a user interface that includes the information associated with the identified group of patients and/or the information indicating reasons the identified group of patients are similar. In some implementations, the user interface may provide information associated with a phenotypically-annotated group of patients (e.g., the identified group of patients), significant clinical biomarkers associated with the group of patients, new indications for the drug that were identified from the medical data.

In some implementations, a user (e.g., a pharmaceutical company) of ACBP platform 220 may utilize information provided by the user interface to select patients for a next phase of the clinical trials of the drug. This may accelerate a NDA submission for the drug by the pharmaceutical company, may reduce liability for the pharmaceutical company due to more informed decision making, may reduce clinical trial cost for the pharmaceutical company, and may improve patient compliance.

In some implementations, ACBP platform 220 may utilize information provided by the user interface to automatically make initial contact with the patients the identified group of patients. For example, ACBP 220 may provide a message (e.g., a phone call, an instant message, a text message, an email message, and/or the like), to a device (e.g., a mobile phone, a computer, and/or the like) associated with each patient, indicating that the patient has been selected to participate in further clinical trials of the drug. Such implementations may reduce resources (e.g., computing resources) needed to plan and organize further clinical trials of the drug.

In some implementations, ACBP platform 220 may utilize information provided by the user interface to automatically select a set of patients from the identified group of patients. For example, ACBP platform 220 may select a set of patients, from the identified group of patients, located at a particular geographical location. Such implementations may reduce costs associated with performing an additional clinical trial since the selected patients may be at a particular geographical location.

In some implementations, ACBP platform 220 may utilize information provided by the user interface to automatically schedule a meeting with the patients from the identified group of patients. For example, ACBP platform 220 may provide a calendar invite (e.g., via an instant message, a text message, an email message, and/or the like), to a device associated with each patient, indicating that the patient is scheduled for a meeting regarding the clinical trial. Such implementations may reduce resources (e.g., computing resources) needed to plan and organize further clinical trials of the drug.

In some implementations, ACBP platform 220 may utilize information provided by the user interface to automatically complete some paperwork regarding the clinical trial of the drug. For example, ACBP platform 220 may automatically complete paperwork associated with the NDA for the drug. Such implementations may reduce resources (e.g., computing resources) needed to seek approval of the drug by automatically performing functions inefficiently performed by other systems.

In some implementations, ACBP platform 220 may utilize information provided by the user interface to automatically plan a next phase of the clinical trial for the drug. For example, ACBP platform 220 may determine what tests and procedures need to be performed for the next phase of the clinical trial. Such implementations may reduce resources (e.g., computing resources) needed to plan and organize further clinical trials of the drug.

In this way, ACBP platform 220 may provide information identifying the group of patients and the information indicating why the group of patients are similar.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Some implementations described herein provide an ACBP platform that determines patient profiles that are likely to respond well to a drug, and tailors clinical trials to target patients with the patient profiles. The ACBP platform may utilize genomic profiles and EMR data of potential patients to identify clinical biomarkers in pre-clinical trial and post-clinical trial settings. The ACBP platform may identify profiles of responsive patient subgroups during clinical trials, may accelerate NDA submissions, may reduce liability due to more informed decision making, may reduce clinical trial cost, may improve patient compliance, may conserve resources (e.g., medical resources, equipment resource, etc.) that would be used to duplicate failed clinical trials due to incorrect patient selection, may improve the clinical trial process, and/or the like.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
one or more memories; and
one or more processors, communicatively coupled to the one or more memories, to:
receive medical data associated with potential patients for a clinical trial of a drug,
the medical data including one or more of:
multi-omics data associated with the potential patients,
genomic profiles of the potential patients,
dosage and time associated with the drug,
electronic medical records of the potential patients, or
clinical trial data associated with the drug;
perform, in parallel, a topological data analysis, a non-matrix factorization analysis, and a neural network analysis of the medical data,
the topological data analysis including utilizing selected metrics to determine a similarity between two nodes in a cluster of nodes associated with the potential patients that is based on a shape or a topology of the cluster,
the non-matrix factorization analysis including a non-negative matrix factorization technique, and
the neural network analysis including a variational graph autoencoders technique that provides unsupervised learning on graph-structured data,
the variational graph autoencoders technique selecting genomic and genetic features of the potential patients and utilizing the genomic and genetic features of the potential patients to generate a graph structure of patient samples;
train a model based on results of performing the topological data analysis, the non-matrix factorization analysis, and the neural network analysis of the medical data;
utilize the trained model to generate patient scores associated with the potential patients;
identify a group of patients, of the potential patients, for the clinical trial of the drug based on applying a weight to a score, of the patient scores, generated utilizing the trained model, wherein different weights are applied to results of each analysis of the medical data;
provide information identifying the group of patients for the clinical trial of the drug;
annotate the information identifying the group of patients with phenotypic data associated with the genomic and genetic features;
identify, based on the annotated information identifying the group of patients, factors that are responsible for identification of the group of patients;
correlate the factors with activity of the drug to determine information indicating reasons the group of patients are similar; and
provide the information indicating reasons the group of patients are similar to use for the clinical trial of the drug.

2. The device of claim 1, where the one or more processors are further to:
preprocess the medical data to generate normalized and dimensionally reduced medical data; and
the one or more processors, when performing, in parallel, the topological data analysis, the non-matrix factorization analysis, and the neural network analysis, are to:
perform, in parallel, the topological data analysis, the non-matrix factorization analysis, and the neural network analysis of the normalized and dimensionally reduced medical data.

3. The device of claim 2, where the one or more processors, when preprocessing the medical data, are to:
normalize the medical data, to generate normalized medical data, by converting one or more formats of the medical data; and
dimensionally reduce the normalized medical data, based on a t-distributed stochastic neighbor embedding technique or an autoencoder technique, to generate the normalized and dimensionally reduced medical data.

4. The device of claim 1, where the one or more processors, when identifying the factors that are responsible for identification of the group of patients, are to:
utilize a supervised learning technique to identify the factors that are responsible for identification of the group of patients.

5. The device of claim 1, where the information identifying the group of patients includes information identifying clinical biomarkers associated with the group of patients.

6. The device of claim 1, where the one or more processors are further to:
preprocess the medical data to generate normalized medical data; and
the one or more processors, when performing, in parallel, the topological data analysis, the non-matrix factorization analysis, and the neural network analysis, are to:
perform, in parallel, the topological data analysis, the non-matrix factorization analysis, and the neural network analysis of the normalized medical data.

7. A non-transitory computer-readable medium storing instructions, the instructions comprising:
one or more instructions that, when executed by one or more processors, cause the one or more processors to:
receive medical data associated with potential patients for a clinical trial of a drug,
the medical data including at least two of:
multi-omics data associated with the potential patients,
genomic profiles of the potential patients, dosage and time associated with the drug,
electronic medical records of the potential patients, or
clinical trial data associated with the drug;
perform a topological data analysis, a non-matrix factorization analysis, and a neural network analysis of the medical data,
at least two of the topological data analysis, the non-matrix factorization analysis, or the neural network analysis of the medical data to be performed in parallel,
the topological data analysis including utilizing selected metrics to determine a similarity between two nodes in a cluster of nodes associated with the potential patients that is based on a shape or a topology of the cluster,
the non-matrix factorization analysis includes a non-negative matrix factorization technique, and
the neural network analysis including a variational graph autoencoders technique that provides unsupervised learning on graph-structured data,
the variational graph autoencoders technique selecting genomic and genetic features of the potential patients and utilizing the genomic and genetic features of the potential patients to generate a graph structure of patient samples;
train a model based on consensus results generated by performing the topological data analysis, the non-matrix factorization analysis, and the neural network analysis of the medical data;
utilize the trained model to generate patient scores associated with the potential patients;
identify a group of patients, of the potential patients, for the clinical trial of the drug based on applying a weight to a score, of the patient scores, generated utilizing the trained model, wherein different weights are applied to results of each analysis of the medical data;
provide information identifying the group of patients for the clinical trial of the drug;
annotate the information identifying the group of patients with phenotypic data associated with the genomic and genetic features;
identify, based on the annotated information identifying the group of patients, factors that are responsible for identification of the group of patients;
correlate the factors with activity of the drug to determine information indicating reasons the group of patients are similar; and
provide the information indicating reasons the group of patients are similar to use for the clinical trial of the drug.

8. The non-transitory computer-readable medium of claim 7, where the instructions further comprise:
one or more instructions that, when executed by the one or more processors, cause the one or more processors to:
preprocess the medical data to generate normalized and dimensionally reduced medical data; and
perform, in parallel, the topological data analysis, the non-matrix factorization analysis, and the neural network analysis of the normalized and dimensionally reduced medical data.

9. The non-transitory computer-readable medium of claim 8, where the one or more instructions, that cause the one or more processors to preprocess the medical data, cause the one or more processors to:

normalize the medical data, to generate normalized medical data, by converting one or more formats of the medical data; and
dimensionally reduce the normalized medical data, based on a t-distributed stochastic neighbor embedding technique or an autoencoder technique, to generate the normalized and dimensionally reduced medical data.

10. The non-transitory computer-readable medium of claim 7, where the one or more instructions, that cause the one or more processors to identify the factors that are responsible for identification of the group of patients, cause the one or more processors to:
utilize a supervised learning technique to identify the factors that are responsible for identification of the group of patients.

11. The non-transitory computer-readable medium of claim 7, where the information identifying the group of patients includes information identifying clinical biomarkers associated with the group of patients.

12. The non-transitory computer-readable medium of claim 7, where the instructions further comprise:
one or more instructions that, when executed by the one or more processors, cause the one or more processors to:
preprocess the medical data to generate normalized medical data; and
perform, in parallel, the topological data analysis, the non-matrix factorization analysis, and the neural network analysis of the normalized medical data.

13. A method, comprising:
receiving, by a device, medical data associated with potential patients for a clinical trial of a drug,
the medical data including one or more of:
multi-omics data associated with the potential patients,
genomic profiles of the potential patients,
dosage and time associated with the drug,
electronic medical records of the potential patients, or
clinical trial data associated with the drug;
preprocessing, by the device, the medical data to generate normalized and dimensionally reduced medical data;
performing, by the device and in parallel, a topological data analysis, a non-matrix factorization analysis, and a neural network analysis of the normalized and dimensionally reduced medical data,
the topological data analysis including utilizing selected metrics to determine a similarity between two nodes in a cluster of nodes associated with the potential patients that is based on a shape or a topology of the cluster,
the non-matrix factorization analysis includes a non-negative matrix factorization technique, and
the neural network analysis including a variational graph autoencoders technique that provides unsupervised learning on graph-structured data,
the variational graph autoencoders technique selecting genomic and genetic features of the potential patients and utilizing the genomic and genetic features of the potential patients to generate a graph structure of patient samples;
training, by the device, a model based on results of performing the topological data analysis, the non-matrix factorization analysis, and the neural network analysis of the normalized and dimensionally reduced medical data;

utilizing, by the device, the trained model to generate patient scores associated with the potential patients;

identifying, by the device, a group of patients, of the potential patients, for the clinical trial of the drug based on applying a weight to a score, of the patient scores, generated utilizing the trained model, wherein different weights are applied to results of each analysis of the medical data;

providing, by the device, information identifying the group of patients for the clinical trial of the drug;

annotating, by the device, the information identifying the group of patients with phenotypic data associated with the genomic and genetic features;

identifying, by the device and based on the annotated information identifying the group of patients, factors that are responsible for identification of the group of patients;

correlating, by the device, the factors with activity of the drug to determine information indicating reasons the group of patients are similar; and providing, by the device, the information indicating reasons the group of patients are similar to use for the clinical trial of the drug.

14. The method of claim 13, where preprocessing the medical data comprises:

normalizing the medical data, to generate normalized medical data, by converting one or more formats of the medical data; and dimensionally reducing the normalized medical data, based on a t-distributed stochastic neighbor embedding technique or an autoencoder technique, to generate the normalized and dimensionally reduced medical data.

15. The method of claim 13, where identifying the factors that are responsible for identification of the group of patients comprises:

utilizing a supervised learning technique to identify the factors that are responsible for identification of the group of patients.

16. The method of claim 13, where the activity of the drug includes a sensitivity to the drug by the group of patients and a resistance to the drug by the group of patients.

17. The method of claim 13, where the information identifying the group of patients includes information identifying clinical biomarkers associated with the group of patients.

18. The method of claim 13, where the group of patients is identified by comparing outputs of the topological data analysis, the non-matrix factorization analysis, and the neural network analysis to identify clusters of patients which are similar.

19. The method of claim 13, where the topological data analysis determines a similarity between a first patient and a second patient, of the potential patients, based on graph analysis.

20. The method of claim 13, where the non-matrix factorization analysis determines a cluster of similar patients, of the potential patients, based on a similarity of elements in a matrix.

21. The method of claim 13, where the neural network analysis determines a similarity between a first patient and a second patient, of the potential patients, based on a comparison between an input layer and a hidden layer.

22. The device of claim 1, where the non-negative matrix factorization technique includes a group of processes in multivariate analysis and linear algebra where a matrix is factorized into two matrices.

23. The non-transitory computer-readable medium of claim 7, where the non-negative matrix factorization technique includes a group of processes in multivariate analysis and linear algebra where a matrix is factorized into two matrices.

24. The method of claim 13, where the non-negative matrix factorization technique includes a group of processes in multivariate analysis and linear algebra where a matrix is factorized into two matrices.

* * * * *